United States Patent [19]

King et al.

[11] Patent Number: 5,214,150

[45] Date of Patent: May 25, 1993

US005214150A

[54] PREPARATION OF HIGHER ALKYLESTERS OF CARBOXYLIC ACIDS

[75] Inventors: Ian R. King, Kings Lynn, England; Karl L. Krumel, Midland, Mich.; Simon C. Lee, Kings Lynn, England

[73] Assignee: DowElanco, Indianapolis, Ind.

[21] Appl. No.: 724,681

[22] Filed: Jul. 2, 1991

Related U.S. Application Data

[63] Continuation of Ser. No. 477,702, Feb. 9, 1990, abandoned.

[51] Int. Cl.$^5$ ................ C07D 213/73; C07D 213/63
[52] U.S. Cl. .................... 546/297; 546/301; 546/330
[58] Field of Search .............. 546/297, 300, 345

[56] References Cited

U.S. PATENT DOCUMENTS

| | | | |
|---|---|---|---|
| 3,755,339 | 8/1973 | McKendry | 546/297 |
| 3,969,360 | 7/1976 | Freedman | 546/297 |
| 4,108,629 | 8/1978 | McKendry | 71/94 |
| 4,487,933 | 12/1984 | Mixan | 546/302 |
| 4,542,221 | 9/1985 | Jones | 546/345 |
| 4,701,531 | 10/1987 | Adaway | 546/297 |

*Primary Examiner*—Alan L. Rotman
*Attorney, Agent, or Firm*—D. Wendell Osborne

[57] ABSTRACT

Larger ($C_6$–$C_{12}$) esters of substituted 2-pyridinyloxyalkanoic acids, such as 1-methylheptyl (4-amino-3,5-dichloro-6-fluoro-2-pyridinyloxy)acetate, are prepared in high yield and purity by first preparing the methyl or ethyl ester and then transesterifying with a $C_6$–$C_{12}$ alcohol. The methyl or ethyl ester can be prepared by alkylation of an alkali metal salt of 4-amino-3,5-dichloro-6-fluoro-2-pyridinol with methyl or ethyl chloroacetate and the transesterification can be carried out in the presence of a tetraalkyl titanate catalyst.

14 Claims, No Drawings

PREPARATION OF HIGHER ALKYLESTERS OF CARBOXYLIC ACIDS

CROSS-REFERENCE TO RELATED APPLICATION

This is a divisional of application Ser. No. 07/477,702 filed Feb. 9, 1990, now abandoned.

BACKGROUND OF INVENTION

The present invention relates to a method of producing carboxylic acid esters of alcohols containing six or more carbon atoms by first preparing the methyl or ethyl ester and then transesterifying with the desired higher alcohol.

Specific esters of many substituted 2-pyridinyloxyalkanoic acids are conveniently prepared by the alkylation of salts of substituted 2-pyridinols with the corresponding ester of a haloalkanoic acid. For example, specific esters of (4-amino-3,5-dichloro-6--fluoro-2-pyridinyloxy)acetic acid are generally produced by alkylation of an alkali metal 4-amino-3,5--dichloro-6-fluoro-2-pyridinate with the corresponding ester of chloroacetic or bromoacetic acid as disclosed in U.S. Pat. Nos. 3,755,339; 4,542,221; and U.S. Pat. No. 4,701,531. A dipolar, aprotic solvent is sometimes employed. This method, while operable, has the disadvantage when applied to many esters of alcohols other than methanol and ethanol, of producing a product which is difficult to recover from the reaction medium in pure form. As a result, the desired ester products are often obtained in an unsatisfactory yield or with an unsatisfactory purity.

The higher esters of carboxylic acids, such as substituted 2-pyridinyloxyacetic acids including (4-amino-3,5-dichloro-6-fluoro-2-pyridinyloxy)acetic acid, on the other hand, are often more valuable than methyl or ethyl esters. This is because they are less volatile and those that are herbicidal are, in some situations, more effective or more selective in their action.

SUMMARY OF THE INVENTION

It has now been found that desirable higher esters of substituted 2-pyridinyloxyalkanoic acids are obtained in high yield and high purity when the methyl or ethyl ester is first prepared by condensation of an alkali metal salt of a substituted 2-pyridinol with a methyl or ethyl chloroalkanoate or bromoalkanoate and the resulting methyl or ethyl ester of a substituted 2-pyridinyloxyalkanoic acid is transesterified with an alcohol containing six or more carbon atoms.

The process of the invention includes a process for preparing an ester of (4-amino-3,5-dichloro-6--fluoro-2-pyridinyloxy)acetic acid and an aliphatic alcohol optionally containing up to 2 substituents selected from $C_1$-$C_6$ alkoxy, $C_1$-$C_6$ alkylthio, and cyano and having a total of 6-12 carbon atoms, which process comprises preparing a methyl or ethyl (4-amino-3,5--dichloro-6-fluoro-2-pyridinyloxy)acetate intermediate by alkylating an alkali metal salt of 4-amino-3,5--dichloro-6-fluoro-2-pyridinol with methyl or ethyl chloroacette or bromoacetate in a dipolar, aprotic solvent containing medium, recovering said intermediate, and, subsequently, transesterifying with an aliphatic optionally containing up to 2 substituents selected from $C_1$-$C_6$ alkoxy, $C_1$-$C_6$ alkylthio, and cyano and having a total of 6-12 carbon atoms.

Octyl esters, including 1-methylteptyl and 2-ethylhexyl esters and ($C_4$-$C_6$ alkoxy)ethyl and ($C_3$-$C_6$ alkoxy)propyl esters are preferred. 1-Methylheptyl esters are especially preferred. Methyl (4-amino-3,5--dichloro-6-fluoro-2-pyridinyloxy)acetate is preferred as an intermediate. N-methyl-2-pyrrolidinone and N,N-dimethylformamide are preferred dipolar, aprotic solvents.

The process of the present invention produces the desired higher esters in better yield and in a purer state than the known methods. It, furthe., takes advantage of the commercial availability of the methyl and ethyl esters of haloalkanoic acids, such as methyl chloroacetate and ethyl bromoacetate.

DETAILED DESCRIPTION OF THE INVENTION

The process of the present invention can be employed for the preparation of higher esters of a wide variety of carboxylic acids and is especially useful for the preparation of higher esters of substituted 2-pyridinyloxyalkanoic acids. Suitable substituted 2-pyridinyloxyalkanoic acids include, for example, 2-(6-bromo-2-pyridinyloxy)-propionic acid, 3,5-dimethyl--2-pyridinyloxyacetic acid, 3-cyano-5-(trifluoro- methyl)-2-pryidinyloxyacetic acid, 3,5,6-trichloro-2--pyridinyloxyacetic acid, 2-(6-fluoro-3,5-dichloro-2--pyridinyloxy)propionic acid, and 6-methoxy-4--(difluoromethyl)-2-pyridinyloxyacetic acid. Esters of substitued 2-pyridinyloxyacetic acids are most ofter prepared. Esters of (4-amino-3,5-dichloro-6-fluoro-2--pyridinyloxy)acetate are of special interest.

The present method is useful for the preparation of higher esters. Suitable esters include those derived from aliphatic alcohols which optionally contain up to 2 substituents selected from $C_1$-$C_6$ alkoxy, $C_1$-$C_6$ alkylthio, and cyano and which have a total of 6-12 carbon atoms. Examples of such alcohols include dodecanol, 1-methylheptanol, 2,3-dimethyl-5-hexen-1-ol, 2-butoxyethanol, 1-butoxy-2-propanol, 3,4-dimethoxy-butanol, cyclohexanol, 1-hexylthio-2-propanol, 1-cyano-hexanol, and the like. Octyl esters, including 1-methylheptyl and 2-ethylhexyl esters, and ($C_4$-$C_6$ alkoxy)ethyl and ($C_3$-$C_6$ alkoxy)propyl esters are often prepared by the process. 1-Methylheptyl and 2-ethyl-hexyl esters are of special interest.

The process of the present invention, as it relates to the preparation of higher esters of (4-amino--3,5-dichloro-6-fluoro-2-pyridinyloxy)acetate, can be illustrated by the following reaction sequence wherein M represents an alkali metal, X represents chloro or bromo, R represents methyl or ethyl, and R' represents an aliphatic alcohol optionally containing up to 2 substituents selected from $C_1$-$C_6$ alkoxy, $C_1$-$C_6$ alkylthio, and cyano and having a total of 6-12 carbon atoms.

ALKYLATION

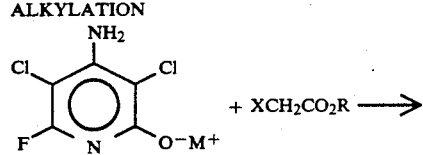

-continued

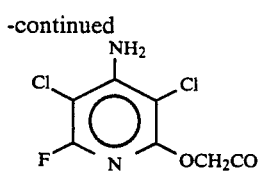
+ MX

TRANSESTERIFICATION

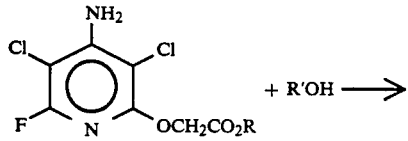
+ R'OH ⟶

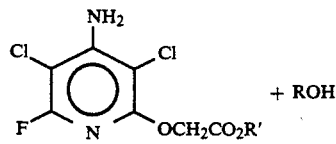
+ ROH

The process details that follow relate to to this embodiment of the invention.

The process is capable of producing the desired higher ester in overall recovered yields of at least about 90 percent of theoretical and of producing, without further purification, a product a: least about 97 percent as pure as the alkali metal salt of 4-amino--3,5-dichloro-6-fluoro-2-pyridinol employed.

The alkylation reaction of the present process as exemplified above involves the alkylation of an alkali metal salt of 4-amino-3,5-dichloro-6-fluoro-2--pyridinol with methyl or ethyl chloroacetate or bromoacetate. This reaction is generally conducted in a dipolar, aprotic solvent, such as N,N-dimethylformamide, N-methyl-2-pyrrolidinone, N,N-dimethylacetamide, 1,3-dimethylimidazolidinone, acetonitrile, sulfolane, dimethyl sulfoxide, acetonitrile, or hexamethyl-phosphoramide (U.S. Pat. No. 3,755,339), in an inert solvent in the presence of a phase transfar catalyst (U.S. Pat. No. 3,969,360), or in water in the presence of a phase transfer catalyst (U.S. Pat. No. 4,701,531). The product obtained is the methyl or ethyl ester of (4-amino-3,5-dichloro-6-fluoro-2-pyridinyloxy)acetic acid. These esters form well defined, relatively high melting crystals which are readily recovered from the reaction medium used for their preparation in high yield and good purity.

It is often preferred to use a dipolar, aprotic solvent medium for this portion of the process. When such a solvent is employed, N,N-dimethylformamide, N-methyl-2-pyrrolidinone, and dimethyl sulfoxide are often preferred. An amount of solvent sufficient to dissolve at least a portion of the alkali metal salt of 4-amino-3,5-dichloro-6-fluoro-2-pyridinol present is generally employed. The system is generally dried to less than about 4 percent water and preferably to less than about 3 percent water before the reaction by distilling out water. The reaction is generally carried out by contacting an alkali metal salt of 4-amino-3,5--dichloro-6-fluoro-2-pyridinol with methyl or ethyl chloroacetate or bromoacetate in the solvent and heating the mixture with agitation. The potassium salt of 4-amino-3,5-dichloro-6-fluoro-2-pyridinol is often the preferred alkali metal salt and methyl chloroacetate is often the preferred haloacetate ester.

Reaction conditions conducive to the alkylation reaction are employed. The haloacetate ester can be employed in an approximately equimolar amount with the pyridinate salt. An excess of haloacetate ester of up to 50 percent is often employed. Excesses of about 2 to about 30 percent are typical. Excesses of about 5 to about 20 percent are often preferred. Alternately, an excess of the pyridinate salt can be employed. The reaction can be carried out at elevated temperatures, usually about 30° C. to about 100° C. and at any convenient pressure. It is typically complete in about 1 to about 24 hours.

The methyl or ethyl ester product of the reaction is typically recovered by adding sufficient water to the mixture, with agitation, to precipitate the desired product and, subsequently, collec:ing the precipitate. This can be done at any convenient temperature, but it is often preferable to make the addition at ambient temperatures or below. It is, however, sometimes preferred to make the addition at elevated temperatures. Temperatures between about 50° C. and about 95° C. are typical. If the addition is made at elevated temperatures, it is preferred to allow the mixture to cool before collecting the precipitate to ensure complete precipitation. The alkali metal halide by-product can be removed before the addition of water, if desired, by conventional means, such as by filtration. It is typically, however, not removed before the addition of water. The amount of water (by weight) added is generally about 0.6 to about 4 times the weight of the dipolar, aprotic solvent present. Amounts of about 0.8 to about 1.8 times the weight of solvent are often preferred. The precipitated ester can be recovered by conventional means, such as filtration or centrifugation, and is typically further extracted with water to remove the solvent as well as any by-product alkali metal halide salt not removed previously. Other methods of recovery, including methods involving evaporation of the solvent, can also be employed.

Methyl or ethyl (4-amino-3,5-dichloro-6--fluoro-2-pyridinyloxy)acetate having over 96 percent purity (on a water and solvent-free basis), usually over 8 percent, can be obtained in the manner described above when the alkali metal salt of 4-amino-3,5--dichloro-6-fluoro-2-pyridinol employed is over 99 percent pure. When an alkali metal salt of 4-amino-3,5--dichloro-6-fluoro-2-pyridinol of lower purity is employed, the purity of the product may be correspondingly lower. Yields of over 90 percent, usually over 93 percent, of that theoretically possible, are generally obtained. The methyl or ethyl ester product obtained is an easily handled crystalline solid.

It is often desirable to purify the methyl or ethyl ester product obtained before proceeding to the transesterification reaction. This can be accomplished by conventional means, for example, by recrystallization from a solvent such as methanol, ethanol, mixtures of water and N-methyl-2-pyrrolidinone, and mixtures of toluene and hexane.

The transesterification reaction of the present process as exemplified above is the transesterification of methyl or ethyl (4-amino-3,5-dichloro-6-fluoro-2--pyridinyloxy)acetate with an aliphatic alcohol optionally containing up to 2 substituents selected from $C_1$–$C_6$ alkoxy, $C_1$–$C_6$ alkylthio, and cyano and having a total of 6–12 carbon atoms. Octyl ($C_8$) alcohols, including 1-methylheptanol (2-octanol), 2-ethylhexanol, and mixed octanols, and ($C_4$–$C_6$ alkoxy)ethanols and ($C_3$–$C_6$ alkoxy)propanols, including 2-butoxyethanol, 1-propoxy-2-propanol and 2-butoxy-1-propanol are preferred alcohols. 1-Methylheptanol and 2-ethylhexanol are especially preferred.

The transesterification can be carried out by any of the known high yield methods of trans-esterification. A catalyst is generally employed. Suitable catalysts include strong acids, such as sulfuric acid, p-toluenesulfonic acid, phosphoric acid, and the like, tetraalkyl titanates, such as tetrabutyl titanate, or their precursors, such as titanium tetrachloride, and tin salts of organic acids. The strong acid may be attached to a cross-linked resin, as in sulfonated polystyrene resins. Tetra($C_1$-$C_{12}$ alkyl) titanates (titanium(IV) $C_1$-$C_{12}$ alkoxides) are preferred catalysts tetrabutyl, tetrapropyl and te:raisopropyl titanates are commercially are available and are often especially preferred.

In carrying out the transesterification step of the process, the methyl or ethyl ester from the first step is typically dried by heating the soiid, by dissolving the moist solid in an inert solvent and removing the water by azeotropic or simple distillation, or by combining the wet solid with the alcohol involved in the transesterification and distilling out the water. The best results are achieved when the mixture is essentially dry before proceeding. Suitable inert solvents are those that do not react appreciably with any of the starting materials or products of the process and that dissolve at least a small amount of the starting ester. Examples include cumene, xylene, decane, and the like. The appropriate alcohol is then combined with the dry mixture, if it is not already present, and finally the catalyst is added. The mixture is generally made to react by heating with agitation and removing the methanol or ethanol by-product obtained by distillation as it forms.

Reaction conditions conducive to the reaction are employed. Generally, an excess of the appropriate alcohol is added for the transesterification. Mole ratios of alcohol to ester of about 2:1 to about 5:1 are typical. A catalytically effective amount of the catalyst is employed. In the case of tetraalkyl titanates, a catalytically effective amount is about 0.01 to about 0.5 percent of the total mixture. The reaction is generally conducted at an elevated temperature, usually about 80° C. to about 200° C. The boiling point of the medium is often a convenient temperature to employ. The pressure of the system is not critical; it may, however, be varied to above or below atmospheric pressure to regulate the boiling point of the medium or to assist in the removal of solvent or excess alcohol.

When the reaction is complete, the desired ester product can be recovered by removing excess alcohol and any other volatiles by distillation so as to obtain the desired ester as a residue. A small amount of the higher alcohol remains, as expected. Most of this higher alcohol can be removed by steam stripping, if desired. Alternatively, the reaction mixture obtained after removal of the methanol or ethanol can be used as is. The catalyst and catalyst by-products can be removed by filtration or centrifugation or by extracting with water, if desired, before or after recovering the product. They can, alternatively, be left in the product. If a strong acid catalyst is employed and is left in the product, it can be neutralized with an appropriate base, if necessary.

A yield of at least about 96 percent of a product that is at least about 97 percent as pure (on an alcohol-free basis) as the methyl or ethyl ester employed as a starting material is generally obtained. Yields of at least about 98 percent of a product that is at least about 98 percent as pure are typical. The actual purity obtained is to a large degree dependent on the completeness of the removal of the excess higher alcohol.

The following examples are presented to illustrate the invention and should not be construed as limitations.

EXAMPLES

Example 1

Preparation of Methyl (4-Amino-3,5-dichloro-6-fluoro-2-pyridinyloxy)acetate in an N,N-Dimethylforamide Medium A solution of 323.0 grams (g) (1.374 moles) of potassium 4-amino-3,5-dichloro-6-fluoro-2-pyridinate in N,N-dimethylformamide weighing a total of 967 g and containing less than 1 percent water was heated to 65° C. and 170.9 g (1.575 moles) of methyl chloroacetate was added over a 30 minute (min) period with stirring. The mixture was heated with stirring at 65° C. overnight and was then filtered at about 55° C. to remove the insoluble salts that formed. The salts were extracted with another 450 milliliters (ml) of N,N-dimethylformamide and the extract was combined with the filtered reaction mixture to obtain a total of 1412 g of solution, which contained no detectable potassium 4-amino-3,5-dichloro--6-fluoro-2-pyridinate. This was cooled to about 0° C. and then 1050 g of water, which had previously been cooled to about 5° C., was added with stirring and cooling over a 30 min period. The mixture was cooled to 0° C. and filtered. The insoluble material collected was extracted with 600 g of cold water. It was then dried and in an oven under reduced pressure to obtain 361.8 g of the title compound which was analyzed and found to be 95.8 percent pure. This corresponds to a yield of 1.29 moles or 93.9 percent of theory. The filtrate and extract water were combined and the volatiles removed by distillation under reduced pressure. A residue of 72.2 g was obtained. This was analyzed and fo:nd to be 13.0 percent the title compound, which corresponds to 0.035 moles or 2.6 percent of theory. There was an insignificant amount of the product in the salts and distillates.

Example 2

Preparation of Methyl (4-Amino--3,5-dichloro-6-fluoro-2-pyridinyloxy)aceate in an N-Methyl-2-pyrrolidinone Medium A 1007.8 g portion of solution of potassium 4-amino-3,5-dichloro-6-fluoro-2-pyridinate in N-methyl--2-pyrrolidinone containing about 20 g of water was diluted with 854 g of additional N-methyl-2--pyrrolidinone in a reaction flask equipped with a distillation head, stirrer, temperature controller, and addition funnel. The mixture was heated with stirring and 39.5 g of volatiles were removed by distillation to obtain 968.3 g of a solution containing 19.7 percent potassium 4-amino-3,5-dichloro-6-fluoro-2-pyridinate (0.812 mole) and about 400 parts per million (ppm) water. This solution was heated at about 40°-45° C. with stirring and 105.6 g (0.973 mole) of methyl chloroacetate and another 137 g of N-methyl-2-pyrrolidinone were added. The mixture was allowed to react for about 16 hours. The excess methyl chloroacetate and other volatiles present were removed by distillation (44.6 g removed). Water (1427 g) was added with stirring at about 80° C. and, after cooling, the solids that formed were collected by filtration to obtain 228.6 g of wet cake containing 90.1 percent of the title compound, 0.3 percent N-methyl-2-pyrrolidinone, and 8.5 percent water. The product was 99.2 percent pure on a dry and solvent free basis. The yield was 94.8 percent of theory.

Example 3

Preparation of 1-Methylheptyl (4-Amino-3,5-dichloro-6-fluoro-2-pyridinyloxy)acetate Methyl (4-amino-3,5-dichloro-6-fluoro-2--pyridinyloxy)acetate (1375 g of 98.0 percent assay, 5.02 moles) was combined with 1901 g (14.6 moles of 1-methylheptanol (2-octanol) in a 5 liter flask equipped with a stirrer, a 30 centimeter (cm) Vigreaux column and distillation head, and a thermometer. The solution was heated to about 130° C. at 10 kiloPascals (kPa) pressure to remove any water present in the system. A 1.3 g portion of tetrabutyl titanate catalyst was added and the mixture was heated at about 150° C. under 60 kPa pressure for 6 hours, distilling out the nethanol as it formed. The pressure was slowly reduced to about 3.3 kPa and the excess 1-methylheptanol was removed by distillation along with any other volatiles. The residue, which amounted to 1857 g, was the title compound. It was found to be 97.4 percent pure and to contain 0.2 percent unreacted methyl ester and 0.1 percent 1-methylheptanol. The yield was, accordingly, 98 7 percent of theory.

Example 4

Preparation of 1-Methylheptyl (4-Amino-3,5-dichloro-6-fluoro-2-pyridinyloxy)acetate A mixture of 50.0 g (0.18 mole) of methyl (4-amino-3,5-dichloro-6-fluoro-2-pyridinyloxy)acetate and 5.0 g of water was combined with 109 g (0.84 mole) of 1-methylheptanol in a 250 ml flask equipped with a thermowell, air-driven stirrer, and 1×20 cm Vigreaux column with a distillation head and a vacuum source. The resulting mixture was heated with stirring at a pot temperature of about 62°-123° C. under about 12-17 kPa pressure and volatiles (mainly water) were removed by distillation until the head temperature reached 113° C. to obtain a dry mixture. There was some foaming. About 0.09 g of tetrabutyl titanate was then added. The mixture was heated with stirring at about 150° C. under about 31 kPa pressure, controlling the heat input so that the head temperature stayed below 60° C. Methanol by-product was removed by distillation as it formed. After 4 hours, 2.7 g of a mixture of methanol and 1-methylheptanol was obtained, which was about 70 percent methanol. The conversion to 1-methylheptyl ester was about 98 percent as determined by gas-liquid chromatography. The temperature was held at about 150° C. and the pressure slowly decreased to about 1.3 kPa to distill out the excess 1-methylheptanol. The temperature was then increased to about 170° C. A total of 76.6 g of 1-methylheptanol was recovered. The residue in the flask amounted to 69.1 g and was found to consist of 1.2 percent 1-methylheptanol and 97.3 percent the desired 1-methylheptyl ester. The yield was, accordingly, 99.6 percent of theory and the purity on an alcohol free basis was 98.5 percent.

What is claimed is:

1. A process for preparing an ester of (4-amino-3,5-dichloro-6-fluoro-2-pyridinyloxy)-acetic acid and an aliphatic alcohol optionally containing up to 2 subustituents selected from $C_1$-$C_6$ alkoxy, $C_1$-$C_6$ alkylthio, and cyano and having 6-12 total carbon atoms, which process comprises preparing methyl or ethyl (4-amino-3,5-dichloro-6-fluoro-2-pyridinyl-oxy)acetate as an intermedite by alkylation of an alkail metal salt of 4-amino-3,5-dichloro-6-fluoro-2--pyridinol with methyl or ethyl chloroacetate or bromoacetate in a dipolar, aprotic solvent containing medium, recovering said intermediate, and, subsequently, transesterifying the intermediate with an aliphatic alcohol optionally containing up to 2 substituents selected from $C_1$-$C_6$ alkoxy, $C_1$-$C_6$ alkylthio, and cyano and having 6-12 total carbtom atoms in the presence of a catalyst selected from a tetra($C_1$-$C_{12}$ alkyl) titanate, titanium tetrachloride, sulfuric acid, p-toluene sulfonic acid, and phosphoric acid.

2. A process according to claim 1 wherein the aliphatic alcohol is an octanol, a ($C_{45}$-$C_6$ alkoxy)ethanol or a ($C_3$-$C_6$ alkoxy)propanol.

3. A process according to Claim 2 wherein the octanol is 1-methylheptanol or 2-ethylhexanol.

4. A process according to Claim 1 wherein a tetra($C_1$-$C_{12}$ alkyl) titanate is employed as the catalyst in the transesterification.

5. A process according to Claim 4 wherein the catalyst is tetrabutyl titanate, tetrapropyl titanate, or tetraisopropyl titanate.

6. A process according to Claim 4 wherein the transesterification reaction mixture is essentially dry when the catalyst is added and the transesterification is conducted at a temperature of between about 80° C. and about 200° C.

7. A process according to Claim 1 wherein methyl or ethyl chloroacetate is employed.

8. A process according to Claim 7 wherein methyl chloroacetate is employed.

9. A process according to Claim 1 wherein the alkali metal is potassium.

10. A process according to Claim 1 wherein the dipolar, aprotic solvent is N-methyl-2-pyrrolidinone, N,N-dimethylformamide or dimethyl sulfoxide.

11. A process according to Claim 10 wherein the solvent is N-methyl-2-pyrrolidinone.

12. A process according to Claim 1 wherein the alkylation is conducted at about 30° C. to about 100° C.

13. A process according to Claim 1 wherein the methyl or ethyl (4-amino-3,5-dichloro-6-fluoro-2--pyridinyloxy)acetate intermediate is recovered by adding water and collecting the precipitate that forms by filtration or centrifugation.

14. A process according to Claim 13 wherein the water is added at about 50° C. to about 95° C. and the mixture is subsequently allowed to cool before collecting the precipitate.

* * * * *